(12) United States Patent
Sutter

(10) Patent No.: US 7,144,395 B2
(45) Date of Patent: Dec. 5, 2006

(54) BIPOLAR TUBULAR SHAFT INSTRUMENT

(75) Inventor: Hermann Sutter, Gundelfingen (DE)

(73) Assignee: Sutter Medizintechnik GmbH, Freiburg (DE)

( * ) Notice: Subject to any disclaimer, the term of this patent is extended or adjusted under 35 U.S.C. 154(b) by 210 days.

(21) Appl. No.: 10/884,645

(22) Filed: Jul. 2, 2004

(65) Prior Publication Data

US 2005/0004571 A1    Jan. 6, 2005

(30) Foreign Application Priority Data

Jul. 3, 2003    (DE) ................................ 103 30 030

(51) Int. Cl.
*A61B 18/18* (2006.01)
(52) U.S. Cl. ............................ 606/51; 606/48; 606/49; 606/50; 606/52
(58) Field of Classification Search ................ 606/48, 606/50–52
See application file for complete search history.

(56) References Cited

U.S. PATENT DOCUMENTS

| | | | |
|---|---|---|---|
| 4,005,714 A * | 2/1977 | Hiltebrandt ................. | 606/51 |
| 4,674,501 A | 6/1987 | Greenberg | |
| 5,174,300 A * | 12/1992 | Bales et al. ................. | 600/564 |
| 5,258,006 A * | 11/1993 | Rydell et al. ................ | 606/205 |
| 5,573,534 A * | 11/1996 | Stone .......................... | 606/48 |
| 5,618,304 A * | 4/1997 | Hart et al. ................... | 606/205 |
| 6,193,718 B1 * | 2/2001 | Kortenbach et al. .......... | 606/50 |
| 6,458,130 B1 * | 10/2002 | Frazier et al. ................ | 606/51 |
| 6,585,735 B1 * | 7/2003 | Frazier et al. ................ | 606/51 |
| 6,669,696 B1 | 12/2003 | Bacher et al. | |
| 2002/0128649 A1 * | 9/2002 | Bacher et al. ................ | 606/46 |
| 2003/0109876 A1 * | 6/2003 | Yamauchi .................... | 606/48 |

\* cited by examiner

*Primary Examiner*—Michael Peffley
*Assistant Examiner*—Alex Toy
(74) *Attorney, Agent, or Firm*—Volpe and Koenig, PC

(57) ABSTRACT

A bipolar tubular shaft instrument (1) has instrument legs (3) and (4), for the operation of which a pull- and/or push rod (6) is axially displaceable within a tube (7). These two parts are insulated relative to one another and are connected to current terminals (11) and (12). For electrically connecting the push rod, a plug pin (15) is provided which is displaceable relative to an opposing contact (14) and engaged therewith. The plug pin (15) is arranged on the push rod (6) neighboring the connecting joint (9) with the actuating handle (10) in generally in a direction of orientation and movement. Thus the contact remains in existence in spite of the movement, and is present in each case upon the instrument legs being closed.

11 Claims, 3 Drawing Sheets

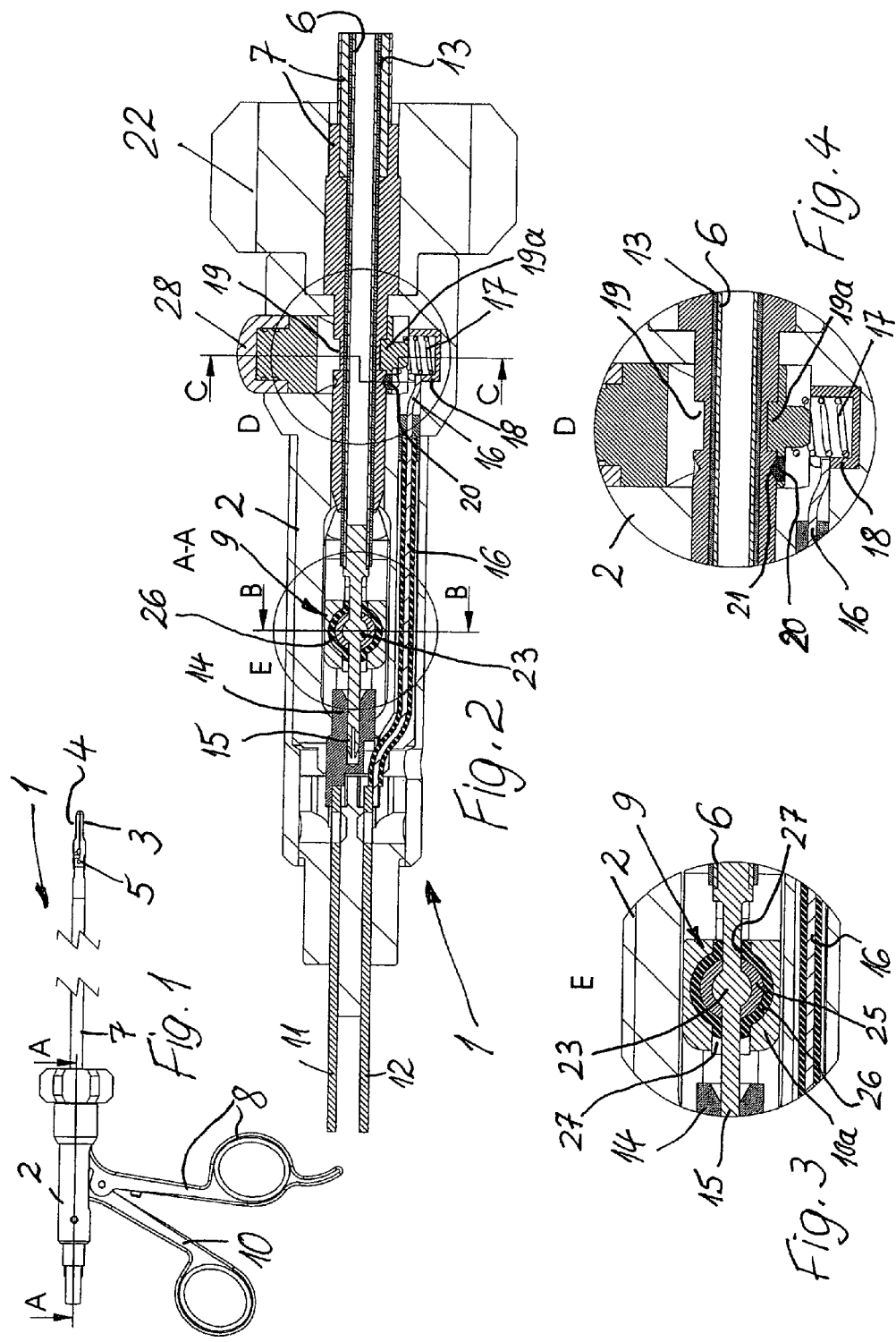

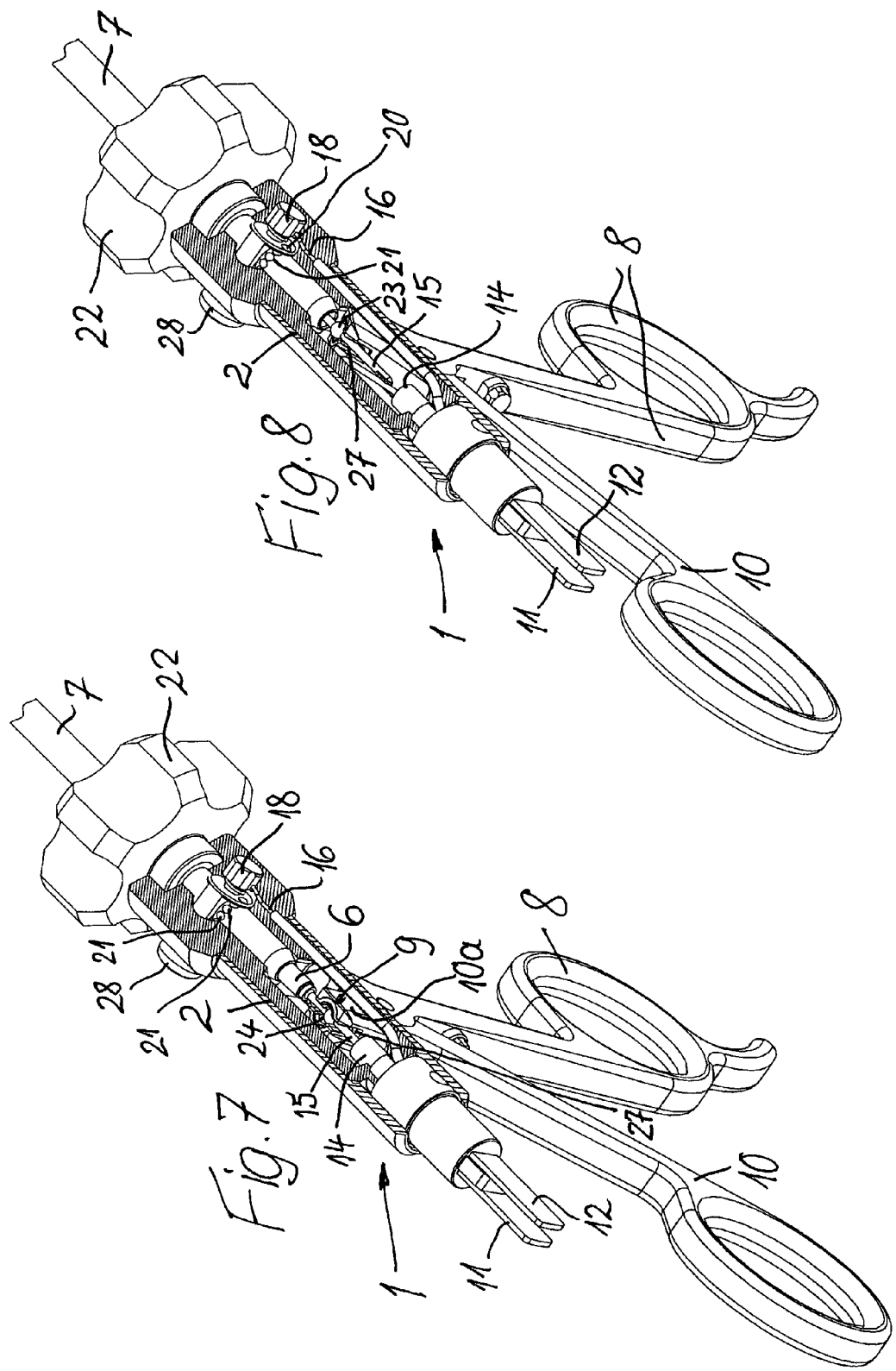

BIPOLAR TUBULAR SHAFT INSTRUMENT

BACKGROUND

The invention relates to a bipolar tubular shaft instrument with a housing portion and two instrument legs, one of which is stationary and the other of which is pivotable about an axis relative to the stationary first leg, or in which both instrument legs are pivotable relative to each other. A pull- and/or push rod engages on the pivotable instrument leg(s) and by means of an axial movement effects the pivoting. A tube, receiving and mounting the push rod, is releasably attached to the housing portion, within which the push rod is movable in the axial direction. A handle is attached to the housing portion and a second handle is provided, pivotable relative thereto, which acts on the push rod by a connecting joint. Two high frequency current terminals are provided, the one current terminal being connected to the push rod and the other current terminal being connected to the tube, and an insulation being provided between the push rod and the tube.

Such tube shaft instruments are known and have proved useful, above all in minimally invasive surgery. According to the configuration of the working portion, and thus above all the instrument leg, and according to the length of the tube shaft, such an instrument may also be used in other operations, for example in open surgery.

Since the problem exists with such bipolar shaft instruments that the tube and the push rod have to be released from the housing portion for their sterilization, the electrical connections or respectively current terminals also have to be broken and released, and on reconnection have to be produced again with such great security that no electrical losses result. With such tubular shaft instruments known heretofore, this leads to expensive solutions which entail difficult mounting.

SUMMARY

The object thus exists of providing an instrument of the kind mentioned at the beginning, with which in spite of the releasability of the tube and push rod, a good electrical contact, secure after many uses, is made possible with at the same time the smallest possible number of individual parts and also the smallest possible dimensions.

This object is attained according to the invention for the bipolar tubular shaft instrument mentioned at the beginning, in that for connnecting the push rod with a current terminal, two contact portions, oriented relative to each other in the direction of longitudinal extension of the push rod, namely a contact bushing and a plug pin in this and displaceable therein, are provided, whose one connecting joint is connected to the push rod and oriented behind its connecting joint in the direction of movement of the push rod, and that the other current terminal of the instrument is fixedly connected to a portion of the instrument, connected in its use position in an electrically conductive manner, directly or indirectly, or in electrically conductive contact.

By a "contact bushing" is to be understood, besides such a bushing having a closed cross section, also such an arrangement in which contact portions, or contact springs, facing each other make it possible to insert a plug pin between them.

The sensitive contact for the push rod is ensured by the solution described above; it may be moved in the axial direction during its use and nevertheless maintains a secure electrical contact. If instead of this a lead forming a loop and connected to the push rod is provided, the push rod can be moved practically freely, leading to an opposite movement between the push rod and the contact bushing, so that electrical contact exists even during the displacement. This represents a simple and space-saving solution with which movements of a lead and its areas that are soldered with instrument portions is avoided.

It is particularly suitable if the plug pin is arranged as an extension of the push rod behind the connecting joint and the contact bushing for this purpose is arranged in the housing portion of the instrument. It is thereby possible to provide the plug pin opposite the connecting joint and thus above all to provide the portion of this connecting joint opposite the plug pin, and the portion of this connecting joint located on the push rod, with such a large cross section that it is insensitive to damage and nevertheless finds sufficient room in a contact bushing or sleeve.

The greatest insertion depth of the plug pin in the contact bushing can correspond to at least about the displacement path of the push rod upon pivoting the instrument leg(s). In this manner, the electrical contact remains retained during the whole displacement movement. It would also be conceivable for the displacement of the plug pin to be somewhat greater than the greatest insertion depth, so that the plug pin leaves the contact bushing in the open position of the instrument and then in this position also, no current can flow. Upon closing the instrument leg, the contact pin then slides without problems into the contact bushing and again makes the contact.

Quite generally, this electrical connection by means of a plug pin and a contact bushing also has the advantage that by the actuation of the instrument these two portions are moved relative to each other, so that the mutual contact always remains in a good state due to the mutual friction. Furthermore, an additional supporting of the push rod results, since the contact bushing and the plug pin can act like a slide bearing.

The other current terminal of the instrument can be connected via a lead to a portion connectable with the tube upon its introduction into its use position, and this portion can in particular be a pressure spring or its mounting in the housing portion, which pressure spring presses a fork-shaped coupling element, displaceable transversely of the tube, into a bare or at least locally bare annular groove of the tube. A thus formed axial coupling of the tube as an annular groove with a fork-shaped opposing-coupling element engaging in this groove is known per se. The previously mentioned design of the invention uses this kind of fastening of the tube and thus confers a double function on this coupling construction, in that by means of this coupling, current contact can also take place to the tube, which is not insulated in the region of the annular groove but is bare, so that the tube also has an electrically conducting connection to the other current terminal. Since the tube performs no axial displacements on the housing portion during use of the instrument, a lead can be provided for this current terminal within the housing portion and can be connected to a corresponding portion, since this lead is exposed to substantially no movement.

The pressure spring acting on the fork-shaped coupling agent can press at the same time against a detent ball which fits into detent recesses in or adjacent to the annular groove of the tube, which is rotatable around its mid-axis. It is known that it can be appropriate during an operation to rotate the tube with the push rod contained therein and the instrument legs. Since such an altered rotational position is to be fixed, however, a latching in preferred rotational positions is advantageous. The arrangement according to the invention makes possible a use of the pressure spring acting for the coupling also for producing the different detent positions.

For axial displacement of the push rod, an enlargement can be arranged on this, forming a portion of the connecting joint and on which the movable handle engages with a recess encompassing this enlargement and forming the connecting joint. The pivoting movement of the movable handle can thereby be converted into the axial displacement movement of the push rod.

The enlargement, particularly a spherical enlargement, which at the same time permits the rotation of the push rod together with the tube relative to the place where the handle is gripped, can be insulated from the handle, so that the user can use the handle without danger even when it consists of metal.

It is appropriate if the enlargement of the push rod is insulated, in that the handle is formed of plastic or that the mounting of the enlargement on the handle includes an insulating material; or that with a mounting of the enlargement in a metal portion when a metal handle is used, an insulation is arranged between the metal portion and the handle. Above all, this last solution results in a high-value instrument with a mounting of the push rod and its spherical enlargement in a counterpart formed of metal with correspondingly high precision; the handle at the same time can also be formed of metal and be machined and guided with corresponding precision. Nevertheless, the required insulation is ensured between the push rod and the handle.

The insulation enclosing the enlargement can overlap the enlargement at the side, and can have a respective open slot toward the side remote from the handle in the region where the push rod passes through, on the one hand, and the region of the electrical contact portion or contact pin, on the other hand. Thus the handle and the recess provided on it can be pivoted relative to the push rod, since this and its contact portion or contact pin engages in corresponding slots, which are pivoted relative to the push rod. At the same time, this pivoting effects a corresponding displacement of the spherical enlargement and thereby of the push rod.

The insulation can be fastened by adhesion to the fork-shaped holding portion of the handle which encloses the spherical enlargement and for its part has in its interior a correspondingly rounded contour matched to the spherical enlargement.

The pivotable handle can be pivotable away from the fixed handle beyond the use position, so that the open end of the connecting joint remote from it, or respectively the recess, enclosing the enlargement, is oriented generally in the direction of the tube. In this position, the push rod can be drawn out in its axial direction from the tube, because the spherical enlargement can then also come out from the fork-shaped holding portion and the recess provided therein of the pivotable handle. Thus the dismantling of the push rod, and likewise its introduction into the use position, are very easy, since the pivotable handle has to be brought into a corresponding strongly pivoted position, so that its fork-shaped holding portion has the corresponding orientation within the housing portion of the instrument, permitting the entry and exit of the spherical enlargement on the one hand and the passage of the contact pin through the corresponding elongated slot on the other hand.

The fork-shaped coupling element for engaging in the annular groove of the tube can be disengaged by a key or the like from the coupling position against the force of the pressure spring. Thus the mounting and demounting of the tube is also very easy.

Above all, by combination of individual or plural of the features and measures described hereinabove, a bipolar tube shaft instrument results, for example a bipolar tube shaft forceps, with which a reception contacting is present which unites the different functions and by the multiple functions keeps the number of individual parts small, which favors economical production. A compact construction with correspondingly small dimensions and the smallest possible weight is possible. The insulation can be arranged in an advantageous manner within the connecting element, so that metal handles do not come into contact with electrical current. The handles can have forms correspondingly adapted to use in various surgical disciplines.

BRIEF DESCRIPTION OF THE DRAWINGS

An exemplary embodiment of the invention is described below using drawings, which are partially schematic.

FIG. 1 is a side view of a bipolar tube shaft instrument according to the invention with two instrument legs, of which one is pivotable relative to the other; the instrument legs are shown in the closed position.

FIG. 2 is an enlarged scale, longitudinal section of the instrument taken along the line A—A through the embodiment of the electrical contacts between current terminals and a push rod for actuating the instrument legs on the one hand, and also a tube receiving these within it on the other hand.

FIG. 3 is an enlarged representation of the detail denoted by E in FIG. 2, namely of the section through the connecting joint between a pivotable handle of the instrument and the push rod.

FIG. 4 is an enlarged representation of the detail denoted by D in FIG. 1, namely a section through the releasable fastening of the tube receiving the push rod within it, with the connection of an electrical lead to a bushing receiving the pressure spring of the counter-coupling element and in electrical contact therewith.

FIG. 7 is a diagrammatic view, partially cut away, of the tube shaft instrument according to the invention in the region of its high frequency current terminals and their connection to the push rod on the one hand and to the tube on the other hand, there being seen at the same time the connecting joint for the jointed connection between the pivotable handle and the push rod, and FIG. 8 is a diagram corresponding to FIG. 7, in which the pivotable handle is pivoted so far that the contact pin located on the push rod has come out of the counter-contact bushing enclosing it in the use position and the recess receiving in itself the spherical enlargement of the connecting joint is oriented so far in the direction of the tube that the push rod with its spherical enlargement can be drawn out in the axial direction or, vice versa, introduced again.

DETAILED DESCRIPTION OF THE PREFERRED EMBODIMENTS

Figure 6:
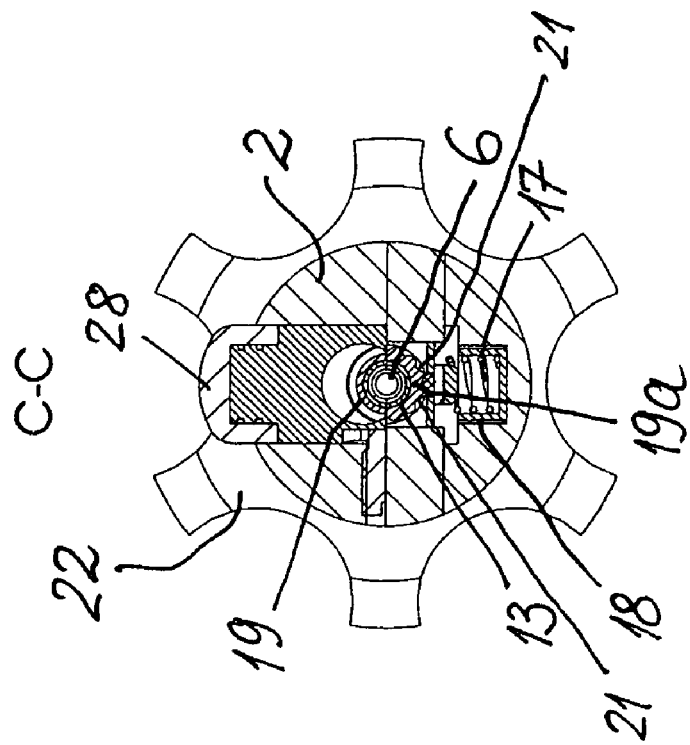
FIG. 6 is a cross sectional view through the mounting and coupling of the tube according to the line C—C in FIG. 2.

A bipolar tubular shaft instrument denoted generally by 1 and also termed "instrument" for short hereinafter is shown and has a housing portion 2, easily visible in FIGS. 2, 7 and 8, and two instrument legs 3 and 4, one instrument leg 3 being stationary and the other instrument leg 4 being pivotable about an axis 5 in a known manner relative to the stationary first leg 3.

It would however also be conceivable that the two legs 3 and 4 can be pivoted relative to each other.

For the movement of the instrument leg(s), in a known manner a pull or push rod 6 is displaceably provided, hollow in the exemplary embodiment, in the housing portion 2, engaging in a known manner on the pivotable instrument legs and effecting the pivoting by the axial movement.

Furthermore a tube 7 receiving and mounting the pull or push rod 6 is releasably fastened to the housing portion 2, with the pull rod or push rod 7 movable in the axial direction therewithin. Both a pull rod and a push rod are concerned, since the to and fro movement in the direction of axial extension effects the pivoting movement of the instrument leg 4 in the opposite sense.

Figure 5:
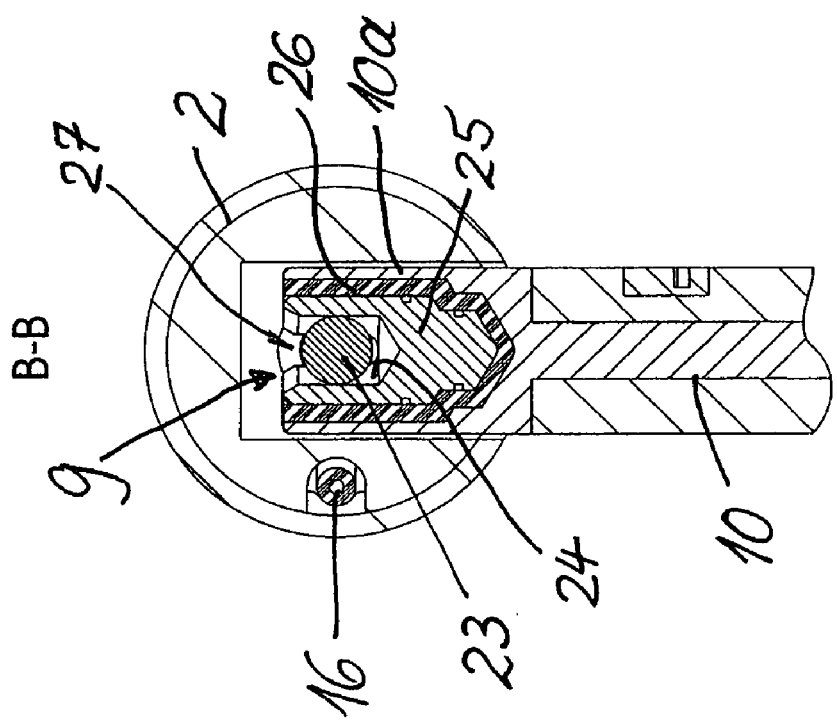
FIG. 5 is a cross sectional view through the insulated connecting joint according to the line B in FIG. 2.

According to FIGS. 1, 7 and 8, a handle 8 is fastened to the housing portion 2 and also a second handle 10 is mounted pivotably relative thereto which acts on the push rod 6, via the connecting joint 9, generally denoted by E as shown in FIG. 3 and clearly shown in the cross section according to FIG. 5. The user can thus grip the two handles 8 and 10 and, by pivoting the handle 10 relative to the handle 8, displace the push rod in a manner still to be described in the axial direction within the tube 7, whereby the instrument leg 4 is pivoted.

On the housing portion 2 there can be seen, above all in FIGS. 1, 2, 7 and 8, two high frequency current terminals 11 and 12 in the form of flat metal projections, the one current terminal 11 being electrically connected in a manner to be described, directly or indirectly to the push rod, and the other current terminal 12 to the tube 7. It can be seen in FIGS. 2 and 4 that between the push rod 6 and tube 7, one of these two parts is provided with electrically separating insulation 13, which is connected to the push rod 6 here.

There can be seen above all from FIG. 2, and also partially in FIGS. 3, 7 and 8, that for providing electrical contact between the push rod 6 with the one current terminal 11, two contact portions are provided oriented relative to one another in the longitudinal extension and movement direction of the push rod 6, namely there are provided a contact bushing 14 and a plug pin 15 insertable and displaceable in the bushing 14. The plug pin 15 is provided, slotted for improvement of the mutual contact. One of these parts, the plug pin 15 in the exemplary embodiment, is connected to the—suitably hollow—push rod 6 and oriented behind its connecting joint 9 in the movement direction of the push rod 6. This contact portion, and thus the plug pin 15, thus forms an extension of the push rod 6 on the side of the connecting joint 9, which is located opposite the actual push rod 6.

According to FIG. 2, the contact bushing 14 is connected to the current terminal 11 and arranged coaxially with the plug pin 15 in the housing portion 2 of the instrument 1, so that upon movement of the push rod 6, the contact pin 15 slides back and forth within the contact bushing 14 and the electrical connection can be maintained in spite of the movement of the push rod 6. The greatest insertion depth of the plug pin 15 into the contact bushing 14 generally corresponds to the displacement path of the push rod 6 on pivoting the instrument leg(s), so that at least during the major portion of the closing motion of the instrument legs 3 and 4 there is also electrical contact. With closed instrument legs 3 and 4 according to FIG. 1, the greater insertion depth of the plug pin 15 in the contact bushing 14 and thereby attains the best possible electrical contact.

The other current terminal 12 of the instrument 1 is fixedly connected to a portion of the instrument 1 which is directly or indirectly connected with the tube 7 in the use position, electrically conductively, or in electrically conductive contact. It can be seen in FIGS. 2 and 4, and also partially in FIGS. 7 and 8, that this other current terminal 12 of the instrument 1 is connected to a part connectable to the tube 7 upon its introduction into its use position, which is fixedly installed within the housing portion 2. In the exemplary embodiment, this portion is a pressure spring 17 or respectively its mounting 18 in the form of a bushing, which is mounted in the housing portion 2 according to FIGS. 2, 7 and 8. The pressure spring 17 acts, according to FIGS. 4 and 6, on a fork-like coupling element 19a which presses in the use position into a bare annular groove 19 of the tube 7; in the exemplary embodiment the tube 7 is provided in two parts, and its portion which in use is inside the housing portion 2 has the annular groove 19, as can easily be seen in FIG. 2. Such an annular groove 19 in the end region of the tube 7 for cooperation with a fork-shaped coupling element 19a is known per se for the releasable mounting of the tube 7.

Via the electrical lead 16, the current can thus be conducted from the current terminal 12 to the mounting 16 and from there via the pressure spring and the likewise electrically conductive fork-shaped coupling element 19a to the bare annular groove 19 and thereby into the tube 7, all of these parts being electrically conductive and also contacting each other under pressure, which leads to good contacting and current transmission.

It can be seen in FIGS. 2, 4 and 6 that the pressure spring 17, which acts on the fork-shaped coupling element 19a and presses into the annular groove 19, at the same time presses against a detent ball 20 arranged axially near this coupling element 19 and fitting into the detent depressions 21 of the tube 7 which is rotatable around its mid-axis. The detent depressions 21 which are provided at the periphery of the tube adjacent to each other can be seen in FIG. 6. Thus the tube 7 can be brought into different rotary positions using a rotary handle 22 and kept in these, the pressure spring 17 having a double function, in which on the one hand it effects the axial fixing of the tube 7 and on the other hand effects the mounting in different rotational positions.

For axial displacement of the push rod 6, a spherical enlargement 23 is arranged on the push rod 6 in the exemplary embodiment; the movable handle 10 includes a recess 24 (FIG. 5) which engages with and around this enlargement 23, so that the connecting joint 9 is formed substantially by this enlargement 23 and the recess 24. This is seen particularly clearly when FIGS. 3 and 5, and also FIGS. 7 and 8, are viewed together.

It can also be clearly seen, in FIGS. 3 and 5, how the spherical enlargement 23, which at the same time permits the rotation of the push rod 6 together with the tube 7 relative to the place of action of the handles 8 and 10 and the housing portion 2, is insulated against the handle 10, namely in that the enlargement 23 is mounted in a metallic portion 25 which also contains the recess 24, and that between this metallic portion 25 and the handle 10, or respectively, an insulation 26 is arranged to the end region 10a containing this metallic portion 25, which according to FIGS. 3 and 5 completely encloses the metallic portion 25.

Thus the handle 10 can be formed of metal, and there results a precise retention and mounting, moreover with good insulation, which however can be arranged in the smallest space, saving space. The insulation 26 is according to FIG. 5 somewhat bucket-shaped and open to the same side—upward in FIG. 5—as the recess 24.

The metallic portion 25 and the insulation 26 laterally surround and cover the enlargement 23 according to FIG. 5 and have, in the region of the places where the push rod passes through on the one hand, and the region of the electrical contact portion, thus of the plug pin on the other hand, a slot 27 which is open on the side remote from the handle 10, so that the enlargement 23 and the push rod 6 can be lifted out with the plug pin 15 out of the recess 24 and thus out of the metallic portion 25 and its insulation 26. In the use position, this is however prevented by the corresponding retention of the push rod in the tube 7 and in the contact sleeve 14.

In order to be able to also release the push rod 6 from its connecting joint 9, the pivotable handle 10 according to FIG. 8 can be pivoted away over the use position from the fixed handle 8, so that the end of the connecting joint 9 open remote therefrom and encompassing the enlargement 23, and thus the recess 24 and the slot 27, are oriented about in the direction of the tube, as can be clearly seen in FIG. 8. In this position, the push rod can thus be pulled out axially from the housing portion 2, because the spherical enlargement 23 can slide out of the recess 24, since this recess 24 is pivoted by the strong pivoting of the handle 10 into the corresponding position, in which the mid-axis of this recess 24 runs practically coaxial, or at a sufficiently acute angle, to the tube 7. Since the recess is provided with the slot 27, the contact pin 15 can also moved away from, and relative to, the metallic portion 26. In the reverse direction, the push rod 6 can thus also be coupled again to the handle 10 and its region 10a having the recess 24.

It should be mentioned that for a stable form of the connecting joint 9, the insulation 26 can be connected by adhesive to the fork-shaped retaining portion of the handle 10 and also to the metallic portion 26.

It can further be seen in FIGS. 2, 4, 6, 7 and 8 that the fork-shaped coupling element 19a, for engagement in the annular groove 19 of the tube 7 can be pulled out of the coupling position against the force of the pressure spring 17 by means of a key 28; this key 28 can act on the fork-shaped annular groove 19 and also adjacent thereto. In the Figures, the coupling element 18a on both sides of the tube 7 in the region of the annular groove 19 is respectively shown.

This key 28 is furthermore insulated because the electrical connection of the tube 7 to the current terminal 12 is provided in its region.

The bipolar tube shaft instrument 1 has instrument legs 3 and 4 which are movable relative to one another. For their actuation, a pull and/or push rod 6 is axially displaceable within the tube 7; these two parts are insulated relative to one another and are connected to current terminals 11 and 12. For contacting the push rod 6, a plug pin 15 is provided which is displaceable relative to, and engaging in, a counter-contact 14, the plug pin 15 preferably being arranged on the push rod 6 in its orientation and contact direction adjacent to the connecting joint 9 with an actuating handle 10. Thus the contact exists in spite of the movement and is present in each case with closed instrument legs.

The push rod 6 is connected, also electrically conductively, in a known manner to one of the instrument legs, while the other instrument leg is in electrically conductive connection to the tube 7, the two instrument legs 3 and 4 being insulated from one another.

The invention claimed is:

1. Bipolar tubular shaft instrument (1) comprising a housing portion (2) and two instrument legs (3, 4), one of which is stationary and the other pivotable about an axis (5) relative to the stationary first leg (3), or in which both instrument legs (3, 4) are pivotable relative to one other, with a pull-and/or push rod (6) which engages the at least one pivotable instrument leg and by an axial movement effects the pivoting, a tube (7), releasably attached to the housing portion (2), receiving and mounting the push rod (6), and within which the push rod (6) is received and is movable in an axial direction, and a first handle (8) attached to the housing portion (2) and a second handle (10), pivotable relative to the first handle (8) that acts on the push rod (6) through a connecting joint (9), first and second high frequency current terminals (11, 12), the first current terminal (11) being connected to the push rod and the second current terminal (12) being connected to the tube (7), and an insulation (13) provided between the push rod and the tube; for electrically connecting the push rod (6) with the first current terminal (11), two contact portions are provided, oriented relative to each other in a direction of longitudinal extension of the push rod (6), the one contact portion comprising a contact bushing (14) and the other contact portion comprising a plug pin (15) which can be plugged into the contact bushing and is displaceable therein, the one contact portion is connected to the push rod (6) and oriented behind the connecting joint (9) in a direction of movement of the push rod (6), and the second current terminal (12) is fixedly connected to a portion of the instrument (1) which in a use position is electrically conductively, directly or indirectly, connected to, or in electrical conductive contact with, the tube (7), wherein a greatest insertion depth of the plug pin (15) in the contact bushing (14) corresponds to at least approximately a displacement path of the push rod (6) upon pivoting of the at least one instrument leg.

2. Instrument according to claim 1, wherein the plug pin (15) is arranged in an extension of the push rod (6) behind the connecting joint (9) and the contact bushing (14) is arranged coaxial therewith in the housing portion (2) of the instrument.

3. Instrument according to claim 1, wherein the second current terminal (12) of the instrument (1) is connected via a lead (16) to an instrument portion which can be connected to the tube (7) upon introduction thereof into the use position, and the instrument portion comprises at least one of a pressure spring (17) or a mounting (18) in the housing portion (2), the pressure spring (17) presses a fork-shaped coupling element (19a) in the use position into a conductive portion of an annular groove (19) of the tube (7).

4. Instrument according to claim 3, wherein the at least one of a pressure spring (17) or a mounting (18) acting on the fork-shaped coupling element (19a) simultaneously presses against a detent ball (20) which fits into the annular groove (19) or into a detent depression (21) adjacent to the annular groove (19) of the tube (7), so that the tube is rotatable around a mid-axis thereof.

5. Instrument according to claim 1, wherein for axial displacement of the push rod (6), an enlargement (23) is arranged thereon, upon which the second, movable handle (10) engages with a recess (24) encompassing the enlargement (23) to form the connecting joint (9).

6. Instrument according to claim 5, wherein the enlargement (23) is generally spherical and allows rotation of the push rod (6) together with the tube (7) relative to a point of action of the handle (10), and is insulated with respect to the handle (10).

7. Instrument according to claim 6, wherein the enlargement of the push rod is insulated by at least one of the handle being formed of plastic, the mounting of the enlargement on the handle being formed of an insulating material, or an insulation (26) is arranged between a metallic portion (25) of the enlargement and the handle (10).

8. Instrument according to claim 6, wherein the enlargement of the push rod is insulated by an insulation (26) arranged between a metallic portion (25) of the enlargement (23) and the handle (10) and wherein the insulation (26) enclosing the enlargement laterally covers the enlargement (23) and has a respective open slot (27) toward a side remote from the handle (10) in a region where the push rod (6) passes through on the one hand and the electrical contact portion (15) on the other hand.

9. Instrument according to claim 7, wherein the handle comprises a fork-shaped holding portion (10a) and wherein the insulation on the fork-shaped holding portion (10a) is fastened by adhesion.

10. Instrument according to claim 1, wherein the pivotable handle is pivotable away out over a use position of the fixed handle (8), so that an open end of the connecting joint (9) remote therefrom and encompassing the enlargement (23) is oriented generally in a direction of the tube (7).

11. Instrument according to claim 4, wherein the fork-shaped coupling element (19a) can be pulled back by a key (28) from a coupling position against a force of the at least one of a pressure spring (17) or a mounting (18), for engaging in the annular groove of the tube (7).

* * * * *